(12) United States Patent
Ryan

(10) Patent No.: US 10,098,535 B2
(45) Date of Patent: Oct. 16, 2018

(54) DYNAMIC OPTICAL COHERENCE TOMOGRAPHY DEVICE AND METHOD

(71) Applicant: Edwin Ryan, St. Paul, MN (US)

(72) Inventor: Edwin Ryan, St. Paul, MN (US)

(*) Notice: Subject to any disclaimer, the term of this patent is extended or adjusted under 35 U.S.C. 154(b) by 230 days.

(21) Appl. No.: 14/775,537

(22) PCT Filed: Mar. 13, 2014

(86) PCT No.: PCT/US2014/026733
§ 371 (c)(1),
(2) Date: Sep. 11, 2015

(87) PCT Pub. No.: WO2014/160468
PCT Pub. Date: Oct. 2, 2014

(65) Prior Publication Data
US 2016/0022134 A1    Jan. 28, 2016

Related U.S. Application Data

(60) Provisional application No. 61/780,443, filed on Mar. 13, 2013.

(51) Int. Cl.
*A61B 3/14* (2006.01)
*A61B 3/00* (2006.01)
*A61B 3/10* (2006.01)
*A61B 3/113* (2006.01)

(52) U.S. Cl.
CPC ......... *A61B 3/102* (2013.01); *A61B 3/0025* (2013.01); *A61B 3/0083* (2013.01); *A61B 3/0091* (2013.01); *A61B 3/113* (2013.01); *A61B 3/145* (2013.01)

(58) Field of Classification Search
CPC ..... A61B 3/102; A61B 3/0091; A61B 3/0025; A61B 3/145; A61B 3/113
USPC .......................................................... 351/206
See application file for complete search history.

(56) References Cited

U.S. PATENT DOCUMENTS

2011/0134394 A1    6/2011    Srinivasan et al.
2011/0299034 A1    12/2011   Walsh et al.
2012/0014966 A1    1/2012    Solinger et al.

FOREIGN PATENT DOCUMENTS

WO    WO-2014160468 A1    10/2014

OTHER PUBLICATIONS

International Application Serial No. PCT/US2014/026733, International Search Report dated Jul. 11, 2014, 2 pgs.
International Application Serial No. PCT/US2014/026733, Written Opinion dated Jul. 11, 2014, 5 pgs.
Application Serial No. PCT/US2014/026733, International Preliminary Report on Patentability dated Sep. 24, 2015, 7 pgs.

*Primary Examiner* — Jack Dinh
(74) *Attorney, Agent, or Firm* — Schwegman Lundberg & Woessner, P.A.

(57) ABSTRACT

An imaging device and method is shown to image ocular tissue in motion. Devices and methods include at least one target to align the patient's eye at a desired angular orientation, multiple selectable target locations, and control circuitry to display the target at the multiple target locations and image ocular tissue at each multiple target location.

13 Claims, 2 Drawing Sheets

DYNAMIC OPTICAL COHERENCE TOMOGRAPHY DEVICE AND METHOD

CLAIM OF PRIORITY

This application is a U.S. National Stage Filing under 35 U.S.C. 371 from International Application No. PCT/US2014/026733, filed on Mar. 13, 2014, and published as WO 2014/160468 A1 on Oct. 2, 2014, which claims the benefit of priority under 35 U.S.C. § 119(e) to U.S. Provisional Patent Application No. 61/780,443, filed on Mar. 13, 2013, which are hereby incorporated herein by reference in their entireties.

TECHNICAL FIELD

This invention relates to ocular imaging.

BACKGROUND

Ocular imaging is useful in diagnosis and treatment of a number of conditions. New imaging techniques such as ultrasound imaging, magnetic resonance imaging, confocal microscopy and optical coherence tomography (OCT) are leading to a better understanding of ocular tissue. Every imaging technique includes advantages and disadvantages. For example, ultrasound imaging has poor resolution in comparison to optical coherence tomography, and confocal microscopy does not provide sufficient imaging of depth of tissue. OCT provides up to millimeter depth penetration. Although OCT imaging is useful, improvements are desirable to provide more detailed information to characterize ocular tissue, especially as relates to motion. OCT as currently configured does not show the effect of movement on tissue.

DETAILED DESCRIPTION

Figure 1:
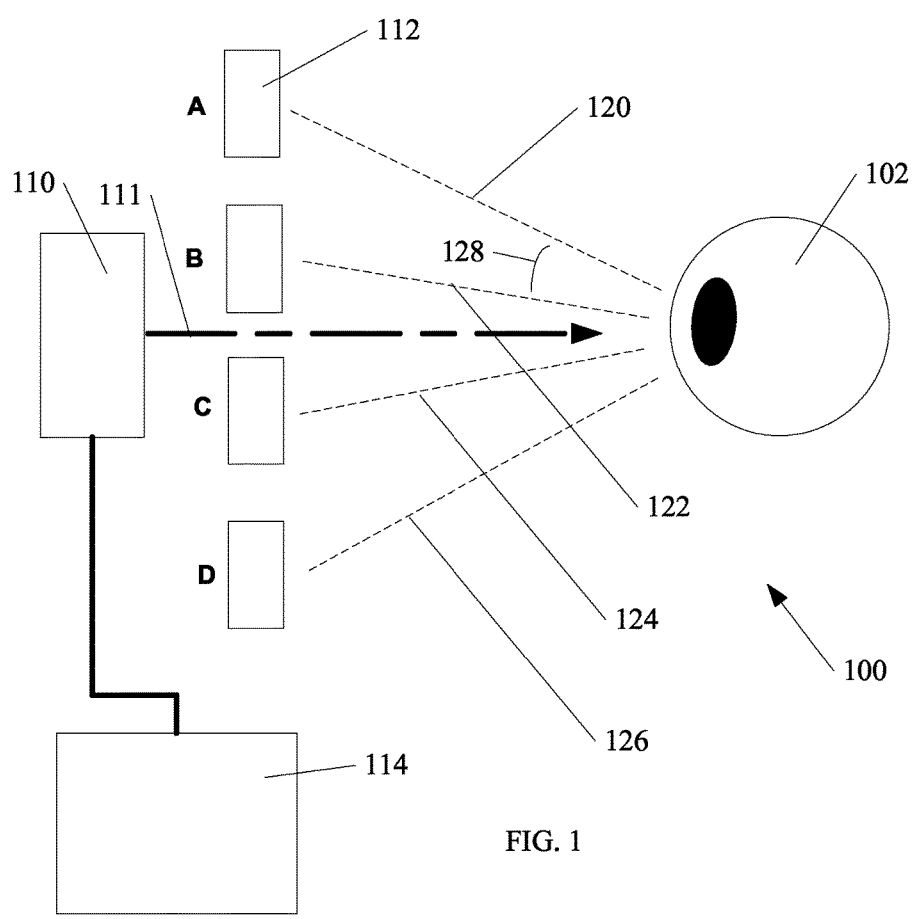
FIG. 1 shows a block diagram of an ocular imaging device according to an embodiment of the invention.
Figure 2:
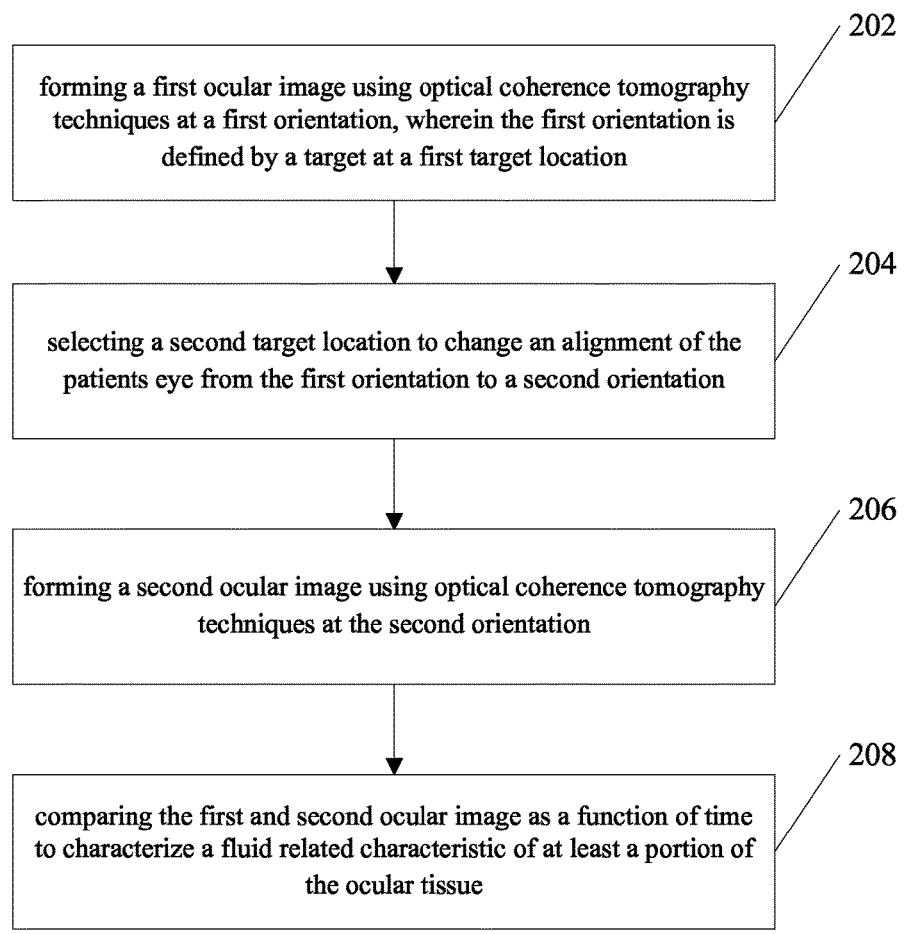
FIG. 2 shows a method of using an ocular imaging device according to an embodiment of the invention.

In the following detailed description, reference is made to the accompanying drawings which form a part hereof, and in which is shown, by way of illustration, specific embodiments in which the invention may be practiced. In the drawings, like numerals describe substantially similar components throughout the several views. These embodiments are described in sufficient detail to enable those skilled in the art to practice the invention. Other embodiments may be utilized and structural, or logical changes, etc. may be made without departing from the scope of the present invention.

FIG. 1 shows an ocular imaging device 100 according to an embodiment of the invention. A patient's eye 102 is shown in relation to other block diagram elements of the device 100. One of ordinary skill in the art, having the benefit of the present disclosure will recognize that any number of possible fixtures such as chin guides, forehead pads, etc. may be used to locate the patient's eye 102 within the device 100.

The device 100 further includes an OCT imaging device 110. The OCT imaging device 110 acquires images of ocular tissue within the patient's eye 102 along imaging direction 111.

The device 100 further includes at least one target 112 to align the patient's eye 102 at a desired angular orientation. FIG. 1 shows four possible targets 112 as an example although, as described below, other examples are also within the scope of the invention. The targets 112 align the patient's eye 102 along the illustrated paths 120-126.

Multiple selectable target locations A-D are also shown in FIG. 1. In one example a single target 112 is movable between the multiple selectable target locations to align the patient's eye 102 along a selected path 120-126. In another example, multiple targets 112 are located at each target locations A-D, and a selected target 112 is activated, while other targets 112 are deactivated. For example, an LED light may be located at each target location A-D, and only a selected LED light is turned on at a time in order to orient the patient's eye 102 along a selected path 120-126.

Control circuitry 114 is further shown in FIG. 1 to display the target at the multiple target locations A-D. In one example, the control circuitry 114 aligns the patient's eye 102 at a desired target location A-D and also signals the OCT imaging device 110 to image ocular tissue at each selected target location A-D.

In operation, by selecting targets 112 at different target locations A-D and imaging at a desired frequency, ocular tissue can be imaged in motion. For example, fixed tissue that is attached to the patient's eye 102, will move with the eye 102 as the target 112 moves. However, more fluid components in the eye 102 will flow, and behave differently when imaged using the dynamic configuration described and shown in FIG. 1.

While a number of advantages of embodiments described herein are listed above, the list is not exhaustive. Other advantages of embodiments described above will be apparent to one of ordinary skill in the art, having read the present disclosure. Although specific embodiments have been illustrated and described herein, it will be appreciated by those of ordinary skill in the art that any arrangement which is calculated to achieve the same purpose may be substituted for the specific embodiment shown. This application is intended to cover any adaptations or variations of the present invention. It is to be understood that the above description is intended to be illustrative, and not restrictive. Combinations of the above embodiments, and other embodiments will be apparent to those of skill in the art upon reviewing the above description. The scope of the invention includes any other applications in which the above structures and fabrication methods are used. The scope of the invention should be determined with reference to the appended claims, along with the full scope of equivalents to which such claims are entitled.

What is claimed is:

1. An ocular imaging device, comprising:
   an optical coherence tomography imaging device;
   at least one target to align the patient's eye at a desired angular orientation;
   multiple selectable target locations; and
   control circuitry to display the target at the multiple target locations and image ocular tissue in motion at each multiple target location.

2. The ocular imaging device of claim 1, wherein the control circuitry is configured to move between the multiple target locations at a frequency sufficient to provide contrast between fixed tissue and viscous ocular components.

3. The ocular imaging device of claim 1, wherein the control circuitry is configured to move between the multiple target locations at a frequency in a range of approximately 10 to 20 locations per second.

4. The ocular imaging device of claim 1, wherein at least two target locations are in a range of approximately four degrees apart.

5. The ocular imaging device of claim 1, wherein a single target is moved between the multiple selectable target locations.

6. The ocular imaging device of claim 1, wherein multiple targets are located at multiple selectable target locations, and wherein during operation, individual targets are activated and deactivated to select a desired target location.

7. The ocular imaging device of claim 1, wherein the control circuitry is configured to activate a pair of target locations that are alternated back and forth.

8. The ocular imaging device of claim 1, wherein the control circuitry is configured to activate a series of target locations n stepwise advancement.

9. The ocular imaging device of claim 1, further including machine readable instructions to generate a movie of ocular motion using images gathered at the multiple selectable target locations.

10. The ocular imaging device of claim 9, wherein the machine readable instructions utilize blood vessel patterns in the patient's eye to align multiple frames within the movie.

11. A method of imaging ocular tissue, comprising:

forming a first ocular image using optical coherence tomography techniques at a first orientation, wherein the first orientation is defined by a target at a first target location;

selecting a second target location to change an alignment of the patients eye from the first orientation to a second orientation;

forming a second ocular image using optical coherence tomography techniques at the second orientation; and comparing the first and second ocular image as a function of time to characterize different tissue motions of the ocular tissue.

12. The method of claim 11, wherein comparing the first and second ocular image as a function of time includes characterizing vitreomacular traction.

13. The method of claim 11, wherein comparing the first and second ocular image as a function of time includes characterizing symptomatic vitreous opacification.

* * * * *

UNITED STATES PATENT AND TRADEMARK OFFICE
CERTIFICATE OF CORRECTION

| | |
|---|---|
| PATENT NO. | : 10,098,535 B2 |
| APPLICATION NO. | : 14/775537 |
| DATED | : October 16, 2018 |
| INVENTOR(S) | : Edwin Ryan |

Page 1 of 1

It is certified that error appears in the above-identified patent and that said Letters Patent is hereby corrected as shown below:

In the Claims

In Column 3, Line 15, in Claim 8, delete "n" and insert --in-- therefor

Signed and Sealed this
Twenty-first Day of April, 2020

Andrei Iancu
*Director of the United States Patent and Trademark Office*